United States Patent [19]

Gartner et al.

[11] Patent Number: 5,506,324
[45] Date of Patent: Apr. 9, 1996

[54] METHOD OF PREPARATION OF CROSSLINKED HYDROPHILIC RESINS

[75] Inventors: Herbert Gartner, Baden-Baden, Germany; Roswitha Petri, Wissembourg, France; Philippe Trijasson, deceased, late of Strasbourg, France, by Fabienne Jeanne Trijasson Heir at Law and Guardian for Florian Trijasson, a minor, Heir at Law

[73] Assignee: The Dow Chemical Company, Midland, Mich.

[21] Appl. No.: 251,826

[22] Filed: May 31, 1994

Related U.S. Application Data

[62] Division of Ser. No. 45,010, Apr. 8, 1993, abandoned.

[30] Foreign Application Priority Data

Apr. 16, 1992 [GB] United Kingdom .................. 9208449

[51] Int. Cl.⁶ ...................................................... C08F 8/00
[52] U.S. Cl. ...................................... 526/318.41; 528/503
[58] Field of Search ........................ 526/318.41; 528/503

[56] References Cited

U.S. PATENT DOCUMENTS

| | | |
|---|---|---|
| 4,076,663 | 2/1978 | Masuda et al. . |
| 4,295,987 | 10/1981 | Parks . |
| 4,654,039 | 3/1987 | Brandt et al. . |

FOREIGN PATENT DOCUMENTS

| | | |
|---|---|---|
| 0205674 | 12/1986 | European Pat. Off. . |
| 0446621 | 9/1991 | European Pat. Off. . |
| 0450923 | 10/1991 | European Pat. Off. . |
| 56-147809 | 11/1981 | Japan . |
| 01159637 | 6/1989 | Japan . |
| 1348234 | 3/1974 | United Kingdom . |
| 1404804 | 9/1975 | United Kingdom . |
| 1263148 | 2/1979 | United Kingdom . |
| 2119384 | 11/1983 | United Kingdom . |
| 2163441 | 2/1986 | United Kingdom . |

Primary Examiner—Bernard Lipman

[57] ABSTRACT

The invention is crosslinked carboxyl containing hydrophilic resin crosslinked by a compound corresponding to formula 1, $$R^1-(O(CH(R^3)CH(R^3)O)_y-C(O)-R^2)_x$$

wherein: $R^1$ is independently is each occurrence a $C_{2-10}$ straight or branched chain alkyl moiety; $R^2$ is independently is each occurrence a $C_{2-10}$ straight or branched chain alkenyl moiety; $R^3$ is independently in each occurrence hydrogen or methyl; x is independently in each occurrence 2 or greater where x is 2; y is independently in each occurrence 3 to 8, and where x is 3 or greater, y is independently in each occurrence 2 to 7.

In another embodiment, the invention is a process for the preparation of crosslinked hydrophilic resins which comprises A) contacting one or more ethylenically unsaturated carboxylic acids, acid arthydrides, and optionally one or more known comonomers with a crosslinking compound of formula 1 in an aqueous medium, optionally in the presence of a free radical or redox catalyst system, under conditions such that a crosslinked hydrophilic resin is prepared. Optionally, the properties of the crosslinked hydrophilic resin are enhanced by heating the crosslinked hydrophilic resin under conditions such that the crosslinked hydrophilic resin exhibits a centrifuge capacity 25 (g/g) or greater, an absorption under load of 25 g/g or greater, and a ratio of absorption under load to centrifuge capacity of 0.6 or greater.

10 Claims, No Drawings

METHOD OF PREPARATION OF CROSSLINKED HYDROPHILIC RESINS

This is a divisional of application Ser. No. 08/045,010 filed Apr. 8, 1993, abandoned.

BACKGROUND OF INVENTION

This invention relates to crosslinked hydrophilic resins, methods for preparing crosslinked hydrophilic resins and absorbent structures incorporating the crosslinked hydrophilic resins.

Hydrophilic resins (also referred to as superabsorbent polymers) are primarily used in personal care products which absorb body fluids, for example baby diapers, adult incontinence products, feminine hygiene products, and the like. In such applications, hydrophilic resin particles are incorporated into absorbent structures which contain for example, synthetic and natural fiber or paper based woven and nonwoven structures, and toughened masses of fibers, such as fluff pads. The materials used in such structures can instantaneously absorb aqueous fluids and distribute them over the whole absorbent structure. The structures, in the absence of hydrophilic resin particles, have limited absorption capacity, and are bulky due to the large amount of material needed to provide acceptable absorption capacity and do not retain fluid under pressure. A means for improving the absorbency and fluid retention characteristics of such absorbent structures is to incorporate hydrophilic resin particles which imbibe fluids to form a swollen hydrogel material, see U.S. Pat. No. 4,610,678 (relevant portions incorporated herein by reference). The hydrophilic resin particles quickly absorb fluids and retain such fluids to prevent leakage and give the absorbent structure a "dry feel" even when wetted.

When the water-absorption capacity of hydrophilic resins is increased, the fraction of water-soluble polymer present in the resin is generally increased. At the same time the gel strength of the swollen gel, its absorption capacity under pressure and absorption speed are reduced. The water absorbent resin tends to agglomerate upon wetting which results in a reduction of its absorption capacity and in gel blockage which prevents transport of fluids within the absorbent structure. This is a particular problem when a large fraction of the absorbent structure is replaced with hydrophilic resin particles to prepare a thin absorbent device.

One method of improving the absorption characteristics is to incorporate a compound which crosslinks the final product into the monomer mixture used to prepare the hydrophilic resin. Brandt U.S. Pat. No. 4,654,039 discloses the preparation of hydrophilic resins and known crosslinking agents for such resins, Column 6 line 34 to Column 7, line 16 (relevant portions incorporated herein by reference). Parks U.S. Pat. No. 4,295,987 discloses the use of ethylene glycol diacrylate, tetraethyleneglycol diacrylate and methylene-bis-acrylamide as crosslinking agents for polyacrylate based hydrophilic resins (relevant portions incorporated herein by reference). Japanese patent 55- 82104 discloses the use of ethylene glycol di(meth)acrylate, trimethylol propane tri(meth)acrylate and propylene glycol di(meth)acrylate as crosslinking agents for polyacrylate based hydrophilic resins (relevant portions incorporated herein by reference). Masuda et al U.S. Pat. No. 4,076,663 discloses a water absorbent resin is produced by polymerizing (A) starch or cellulose, (B) at least one monomer having a polymerizable double bond which is water-soluble or becomes water-soluble by hydrolysis and (C) a crosslinking agent, and subjecting, if necessary, the resulting product to hydrolysis. Disclosed as among useful crosslinking agents are di- or poly-esters of unsaturated mono- or poly-carboxylic acids with polyols such as di- or tri-(meth)acrylic acid esters of polyols (such as ethylene glycol, trimethylol propane, glycerine, polyoxyethylene glycols, polyoxypropylene glycols, and the like (relevant portions incorporated herein by reference).

Crosslinking improves the strength of the hydrophilic resins and improves the retention of absorbed fluids when the hydrophilic resin is placed under a load and reduces the percentage of extractable materials present, but on the other hand results in a lower capacity of the resin and in some areas may require more of the resin to achieve desired absorption capacity. Extractable materials are water soluble oligomers or non-crosslinked polymers which can be extracted from the hydrophilic resins when exposed to aqueous fluids. The presence of extractable materials reduces the efficacy of the water absorbent particles. Many compounds useful as crosslinkers are not water soluble and require the presence of surfactants or dispersants to solubilize or disperse them so they can be present in the reaction medium to crosslink the hydrophilic resins. The presence of such dispersants and surfactants often adversely affect the absorbent properties of the hydrophilic resins.

What are needed are hydrophilic resins which have high absorption capacity, low extractable materials and high toughness or gel modulus. What is further needed is a process for the preparation of such resins. What are needed are crosslinking agents which are water soluble. The properties desired in hydrophilic resin vary depending upon the application and the desired effect of the resins. Thus, what are needed are processes which are flexible in preparing hydrophilic resins with varied properties such as absorption capacity and absorption under load.

SUMMARY OF INVENTION

The invention comprises a carboxyl containing hydrophilic resin crosslinked by one or more compounds corresponding to formula 1

$$R^1\text{—}(O(CH(R^3)CH(R^3)O)_y\text{—}C(O)\text{—}R^2)_x \qquad \text{formula 1}$$

wherein $R^1$ is independently is each occurrence a polyvalent $C_{2\text{-}10}$ straight or branched chain alkyl moiety;

$R^2$ is independently is each occurrence a $C_{2\text{-}10}$ straight or branched chain alkenyl moiety;

$R^3$ is independently is each occurrence a hydrogen or methyl;

x is independently in each occurrence a number of about or greater;

where x is 2, y is independently in each occurrence a number of about 3 to about 8; and where x is 3 or greater, y is independently a number of about 2 to about 7.

In another embodiment, the invention is a process for the preparation of crosslinked hydrophilic resins which comprises A) contacting i) one or more ethylenically unsaturated carboxylic acids, ethylenically unsaturated carboxylic acid anhydrides or salts thereof and optionally ii) one or more comonomers of an acrylamide, a vinyl pyrrolidone, an acrylonitrile, a vinyl sulphonic acid, a cellulosic monomer, modified cellulosic monomer, a polyvinyl alcohol or a starch hydrolyzate with iii) a crosslinking compound corresponding to formula 1 in an aqueous medium, optionally in the presence of a free radical or redox catalyst system, under conditions such that a crosslinked hydrophilic resin is prepared.

In another embodiment the properties of the crosslinked hydrophilic resin may be further enhanced or improved by heating the crosslinked hydrophilic resin under conditions such that the crosslinked hydrophilic resin exhibits a Centrifuge Capacity (CC) of 25 g/g or greater, an Absorption Under Load (AUL) of 25 g/g or greater and a ratio AUL/CC of 0.6 or greater, wherein the heating is performed after the crosslinked hydrophilic resin has been dried and optionally subjected to means to reduce the particle size of the crosslinked hydrophilic resin.

In yet another embodiment, the invention is a water-absorbent structure containing the crosslinked hydrophilic resins of this invention.

BRIEF DESCRIPTION OF THE DRAWINGS

FIG. 1 is the plot of ratio of the percentage of extractable materials to centrifuge capacity against the centrifuge capacity of crosslinked resins having varied amounts of ethylene oxide in the backbone of the crosslinker. FIG. 2 plots both the ratio of centrifuge capacity after post heating (CC(T)) to centrifuge capacity before heating (CC(o)) and Absorption under load after post heating against the number of moles of ethylene oxide in the backbone of the crosslinker. FIG. 3 is a plot of the ratio of centrifuge capacity after post heating to centrifuge capacity before post heating versus post heat temperature. FIG. 4 shows a plot of the ratio absorption under load after post heating to absorption under load before post heating against post heat temperature. FIG. 5 plots the absorption under load against centrifuge capacity at various post heat temperatures. FIG. 6 plots the ratio of absorption under load to centrifuge capacity against centrifuge capacity at each post heat temperature. FIG. 7 plots the level of extractable materials present at each post heat temperature against centrifuge capacity. FIG. 8 plots the ratio of extractables to centrifuge capacity against centrifuge capacity at each post heat temperature. FIG. 9 plots the absorption under load against time for a resin of the invention and a comparative resin. FIG. 10 plots the ratio of the absorption under load at various times to final absorption under load (60 minutes) against time for two resins, one of the invention and one comparative. FIG. 11 is the plot of Absorption under load versus time for two resins, one of the invention and one comparative resin. FIG. 12 plots the ratio of absorption under load at various times over absorption under load at a final time of 60 minutes against time. FIG. 13 plots absorption under load at varying load levels of 0 to 1.0 psi (70.31 gm/cm$^2$) for a resin of the invention and a comparative resin.

DETAILED DESCRIPTION OF THE INVENTION

The hydrophilic resins of this invention demonstrate high absorption capacities while having low extractable material fractions and a high absorbent gel particle toughness. The crosslinkers corresponding to formula 1 are water soluble or self dispersible in water and thus no additional surfactants or dispersants are required. The optional post heating step in the process for the preparation of the water-absorbent resin particles allows variation of the process to achieve a desired mix of properties, that is absorption under load, absorption capacity and percent of extractable materials.

The crosslinked hydrophilic resins of this invention are polymers derived from one or more ethylenically unsaturated carboxylic acids, ethylenically unsaturated carboxylic acid anhydrides or salts thereof. Additionally the polymers may include comonomers commonly known in the art for use in absorbent resins or for grafting onto absorbent resins such as an acrylamide, an acrylonitrile, a vinyl pyrrolidone, a vinyl sulphonic acid, a cellulosic monomer, a modified cellulosic monomer, a polyvinyl alcohol or a starch hydrolyzate. Olefinically unsaturated carboxylic acid and carboxylic acid anhydride monomers include the acrylic acids typified by acrylic acid, methacrylic acid, ethacrylic acid, alpha-chloroacrylic acid, alpha-cyano acrylic acid, beta-methyl-acrylic acid (crotonic acid), alpha phenyl acrylic acid, beta-acryloxy propionic acid, sorbic acid, alpha-chloro sorbic acid, angelic acid, cinnamic acid, p-chloro cinnamic acid, beta-styrl acrylic acid (1-carboxy- 4-phenyl butadiene-1,3), iraconic acid, citraconic acid, mesaconic acid, glutaconic acid, aconitic acid, maleic acid, fumaric acid and maleic acid anhydride. Preferably the starting monomer is acrylic acid, methacrylic acid, or a salt thereof, with acrylic acid or a salt thereof being more preferred.

The compounds corresponding to formula 1 generally are $C_{2-10}$ polyhydric hydrocarbons which have been alkoxylated with between two and eight alkylene oxide units per hydroxyl moiety wherein the terminal hydroxyl moiety of each alkyleneoxide chain is esterified with a $C_{2-10}$ unsaturated carboxylic acid or ester thereof. Preferably the starting alcohol is a $C_{3-6}$ carbon polyhydric compound having from 2–4 hydroxy moieties. Even more preferably the starting material is trimethylol propane, glycerol, pentaerythritol, 1,3 propanediol, propylene glycol, 1,4 butanediol, or butylene glycol. More preferably the starting alcohol is trimethylol propane, glycerol or pentaerythritol with trimethylol propane being most preferred. The alkylene oxide chain may be composed of ethylene oxide, propylene oxide or butylene oxide moieties. Such chain may comprise a single species of a alkylene oxide or a mixture of the alkylene oxide species. If a mixture is used, various alkylene oxides may be arranged in a random pattern or in blocks of each species. Preferably, the alkylene oxide chain is based on ethylene oxide, propylene oxide or a mixture thereof, more preferably it is an ethylene oxide or propylene oxide chain and most preferably an ethylene oxide chain. Preferably each alkylene oxide chain attached to the hydroxy moieties of the starting alcohol have from three to seven alkylene oxide units, and most preferably four to six alkylene oxide units. The preferred number of alkylene oxide units in each chain is dependent upon the number of chains. As the number of chains (x) increase, the number of alkylene oxide units per chain required for good properties is lower. The esterifying agent is a $C_{2-10}$ straight or branched chain ethylenically unsaturated carboxylic acid or ester thereof, preferably a $C_{2-4}$ ethylenically unsaturated carboxylic acid or ester thereof, even more preferably a $C_{2-3}$ ethylenically unsaturated carboxylic acid or ester thereof, and most preferably acrylic acid, methacrylic acid or an ester thereof.

The crosslinkers of this invention are prepared by processes well-known in the art. In particular the polyhydric alcohol is reacted with from 2 to 8 alkylene oxide units per hydroxy moiety so as to prepare a compound with 2 or more chains of hydroxy terminated polyalkylene oxides. Thereafter the reaction product is reacted with sufficient $C_{2-10}$ straight of branched chained ethylenically unsaturated carboxylic acids, or an ester thereof, to provide a terminal ester containing ethylenically unsaturated moiety for each hydroxy moiety on the alkylene chain attached to the starting alcohol. Such preparation procedures are well known in the art, see March, Advanced Organic Chemistry, 2nd Edition, pp. 361–365 (relevant parts incorporated herein by reference). Generally, the crosslinkers described by Formula 1 are found as a mixture of materials described by the formula and by-products resulting from the preparation process. Crosslinkers corresponding to formula 1 are available from Craynor under the trademark Craynor and from Sartomer under the trademark Sartomer.

$R^1$ is preferably a polyvalent $C_{3-6}$ straight or branched chain hydrocarbon. Polyvalent as used herein means the moiety has two or more valences by which the moiety is bonded to other moieties. $R^2$ is preferably a $C_{2-4}$ straight or branched chain alkenyl moiety, and most preferably a $C_{2-3}$ straight or branched chain alkenyl moiety. In one preferred embodiment for each $(CH(R^3)CH(R^3)O)$— unit one $R^3$ is methyl and the other is hydrogen. Most preferably $R^3$ is hydrogen. Preferably, x is from about 2 to about 4, and even more preferably from about 3 to about 4. Preferably, y is from about 3 to about 7 and more preferably about 4 to about 6.

The crosslinker is present in sufficient amounts to significantly improve the absorption under load and reduce the percentage of extractable materials contained in the hydrophilic resin while preferably maintaining or increasing the centrifuge capacity. Preferably the crosslinker is present in an amount of about 1,000 parts per million or greater by weight based on the amount of the polymerizable monomer present, more preferably about 2,000 parts per million or greater and most preferably about 3,500 parts per million or greater. Preferably the crosslinker is present in an amount of about 50,000 parts per million or less by weight based upon the amount of the polymerizable monomer present, more preferably about 5,000 parts per million or less and most preferably about 8,000 parts per million or less.

Conventional additives, which are well known in the art, such as surfactants, may be incorporated into the monomer mixture.

The crosslinked hydrophilic resins are prepared by contacting i) the one or more of an ethylenically unsaturated carboxylic acid, an ethylenically unsaturated carboxylic acid anhydride or a salt thereof, ii) optionally one or more of an acrylamide, a vinyl pyrrolidone, a vinyl sulphonic acid, an acrylonitrile, a cellulosic monomer, a modified cellulosic monomer, a polyvinyl alcohol monomer, or a starch hydrolyzate monomer with iii) a crosslinking compound which corresponds to formula 1 in an aqueous medium, optionally in the presence of a free radical or oxidation reduction (redox) catalyst system under conditions such that a crosslinked hydrophilic resin is prepared. As used herein aqueous medium means water, or water in admixture with a water miscible solvent. Preferred water miscible solvents include lower alcohols, alkylene glycols, and the like. Preferably the aqueous medium is water.

In a preferred embodiment, the from about 10 to about 1000 ppm by weight of chloric, bromic acid or a salt thereof is added to the i monomers, optional ii comonomers and iii crosslinking compound before polymerizaton is started. Chloric acid is preferred and from 200 to 500 ppm by weight of the i monomers, optional ii comonomers and iii crosslinking compound is preferred.

The monomers and crosslinkers are preferably dissolved, dispersed or suspended in the aqueous medium at a concentration level of about 15 percent by weight or greater, more preferably about 25 percent or greater, and most preferably about 29 percent or greater. The monomers and crosslinkers are preferably dissolved, dispersed or suspended in the aqueous medium at a concentration level of about 50 percent by weight or less and more preferably about 40 percent or less. An optional component in the aqueous medium is a conventional water soluble polymerization initiator material including peroxygen compounds such as sodium, potassium and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate and the like. Conventional redox initiator systems can also be utilized which are formed by combining the foregoing peroxygen compounds with reducing agents such as sodium bisulfite, sodium thiosulphate, L-ascorbic acid or a salt thereof, or ferrous salts. If utilized, the initiator material can comprise up to about 5 mole percent based on the polymerizable monomer present. More preferably the initiator comprises from about 0.001 to about 0.5 mole percent based on the polymerizable monomer.

The process of the invention may be performed in a batch manner wherein all of the reaction materials are contacted and the reaction proceeds, or it may take place with the continuous addition of one or more of the components over the reaction period. The aqueous medium is subjected to polymerisation conditions which are sufficient to produce the crosslinked hydrophilic resin of the invention. Preferably, the reaction is performed under an inert gas atmosphere, for example under nitrogen or argon. The reaction may be performed at any temperature at which polymerisation occurs, preferably about 0° C. or greater, more preferably about 25° C. or greater and most preferably about 50° C. or greater. Preferably the temperature is about 100° C. or less, more preferably about 80° C. or less and most preferably about 70° C. or less. The reaction is exothermic and it may be desirable to provide a means for cooling the reactor so as to maintain a desired temperature. The reaction mixture may be reacted for a time sufficient to result in the desired conversion of polymerizable monomer to crosslinked hydrophilic resins. Preferably the conversion is about 95% or greater, more preferably about 98% or greater and most preferably about 99% or greater. Preferably the reaction time is about 20 minutes or greater, more preferably about 1 hour or greater and most preferably about 2 hours or greater. Preferably the reaction time is about 6 hours or less, more preferably about 4 hours or less and most preferably about 3 hours or less. Preferably about 25 mole percent or greater of the carboxylic acid units of the hydrophilic resin are neutralized with base, even more preferably about 50 percent or greater and most preferably about 65 percent or greater. This neutralization may be performed after completion of the polymerisation. In a preferred embodiment the starting monomer mix has carboxylic acid moieties which are neutralized to the desired level prior to polymerisation. The final polymer or the starting monomers may be neutralized by contacting them with a salt forming cation. Such salt forming cations include alkaline metal, ammonium, substituted ammonium and amine based cations. Preferably the polymer is neutralized with an alkaline metal hydroxide such as sodium hydroxide.

It is also possible, however, to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. Polymerization in such procedures still occurs in the aqueous phase, but suspensions or emulsions of this aqueous phase in an organic solvent permits better control of the exothermic heat of polymerization and further provides the flexibility of adding one or more of the aqueous reaction mixture components in a controlled manner to the organic phase.

Inverse suspension polymerization procedures are described in greater detail in Obayashi et al U.S. Pat. No. 4,340,706 (relevant portions incorporated herein by reference) and Flesher et. al. U.S. Pat. No. 4,506,052 (relevant portions incorporated herein by reference). When inverse suspension polymerization or inverse emulsion polymerization techniques are employed, additional ingredients such as surfactants, emulsifiers, polymerization stabilizers and the like may be added to the overall reaction mixture. When any process employing organic solvent is utilized, it is important that the hydrogel-forming polymer material recovered from such processes be treated to remove substantially all of the excess organic solvent. It is highly preferred for example, that the hydrogel-forming polymers herein contain no more than about 0.5% by weight of residual organic solvent.

During polymerisation the crosslinked hydrophilic resins of the invention generally absorb all of the aqueous reaction medium to form a hydrogel. The crosslinked hydrophilic resin is recovered from the reactor in the form of an aqueous hydrogel. Hydrogel as used herein refers to water swollen crosslinked hydrophilic resin particles. In preferred embodiments such hydrogels comprise about 15 percent by weight or greater crosslinked hydrophilic resin, with the remainder comprising water and more preferably about 25 percent by weight or greater, preferably the hydrogel comprises about 50 percent by weight or less of crosslinked hydrophilic resin in water and more preferably about 45 percent by weight or less. The hydrogel is preferably in granular form, with particle sizes of about 2 cm or less being more preferred. In multiphase polymerisation the crosslinked hydrophilic resin hydrogel particles may be recovered from the reaction medium by azeotropic distillation and/or filtration followed by drying. If recovered by filtration then some means of removing the solvents present in the hydrogel must be used. Such means are commonly known in the art.

After removal from the reactor the crosslinked hydrophilic resin hydrogel particles may be optionally subjected to mechanical particle size reduction. The size of the gel particles after mechanical particle size reduction should be such that homogeneous drying of the particles can occur. This particle size reduction can be performed by any means known in the art which gives the desired result. Preferably the particle size reduction is performed by chopping the hydrogel.

Thereafter, the crosslinked hydrophilic resin hydrogel particles are subjected to conditions to remove the water substantially all and optional solvent, such that the water-absorbent resin particles can be further processed, packaged, and incorporated into absorbent structures. The temperature at which the drying takes place is a temperature high enough such that the water, and optional solvent, is removed in a reasonable time period, yet not so high so as to cause degradation of the crosslinked hydrophilic resin, such as by breaking of the crosslink bonds in the resin. Preferably, the temperature of the water absorbent resin particles during drying is about 170° C. or less. Preferably, the temperature during drying is about 100° C. or above, and more preferably about 150° C. or above. The drying time should be sufficient to remove substantially all of the water and optional solvent. Substantially all means all water and optional solvent is removed except minor amounts which do not adversely affect the processing of the particles or their function. Preferably, a minimum time for drying is about 10 minutes or greater, with about 15 minutes or greater being preferred. Preferably the drying time is about 60 minutes or less, with about 20 minutes or less being more preferred. In a preferred embodiment, drying is performed under conditions such that water, and optional solvent, volatilizing away from the absorbent resin particles is removed. This can be achieved by the use of vacuum techniques or by passing inert gases or air over or through the layers of crosslinked hydrophilic resin particles. In a preferred embodiment, the drying occurs in dryers in which heated air is blown through or over layers of the crosslinked hydrophilic resin particles. Preferred dryers are fluidized beds or belt dryers. Alternatively a drum dryer may be used. Alternatively the water may be removed by azeotropic distillation, such techniques are well known in the art.

During drying the crosslinked hydrophilic resin particles may form agglomerates and may then be subjected to mechanical means for breaking up the agglomerates. In a preferred embodiment, the crosslinked hydrophilic resin particles are then subjected to mechanical particle reduction means. Such means can include chopping, cutting and/or grinding. The object is to reduce the particle size of the water-absorbent resin particles to a particle size acceptable in the ultimate end use. In a preferred embodiment, the absorbent resin particles are chopped and then ground. The particle size is preferably about 2 mm or less, more preferably about 0.8 mm or less. Preferably the particles have a size of about 0.02 mm or greater, more preferably about 0.05 mm or greater.

The crosslinked hydrophilic resin particles may be subjected to surface crosslinking techniques to further strengthen the particles. Such techniques are well known in the art see for example GB 2,119,384 (relevant parts incorporated herein by reference).

In a preferred embodiment after drying and particle size reduction, the crosslinked hydrophilic resins are postheated at temperatures at which the crosslinked hydrophilic resins absorption properties are improved. The time period for exposure to such temperatures is chosen such that the absorption properties of the resin are improved. The crosslinked hydrophilic resins are preferably heated to a temperature about 170° C. or above, most preferably about 190° C. or above and most preferably to about 210° C. or above. Below about 170° C. no improvement in the absorption properties is seen. The temperature should not be so high as to cause the crosslinked hydrophilic resin polymer to degrade. Preferably the temperature is about 250° C. or below and most preferably about 230° C. or below. The crosslinked hydrophilic resin is heated to the desired post heat temperature and preferably maintained at such temperature for at least about 1 minute heating time and most preferably at least about 5 minutes. Below about 1 minute no improvement in properties occurs. If the heating time is too long it becomes uneconomical and risk is run that the crosslinked hydrophilic resin may be damaged. Preferably crosslinked hydrophilic resin is maintained at the desired temperature for about 60 minutes or less, preferably about 30 minutes or less. Above about 60 minutes no significant improvement in properties is noticed. The properties of the crosslinked hydrophilic resin can be adjusted and tailored by adjustment of the temperature and the time of the post heating step. Longer post heat times result in a higher absorption under load, a lower level of extractable materials and a lower centrifuge capacity. The use of higher temperatures for the post heat step result in a higher absorption under load, and a lower level of extractable materials and a lower centrifuge capacity. The use of shorter times and lower post temperatures result in higher centrifuge capacities and extractable material level and a lower absorption under load.

After post heating the crosslinked hydrophilic resins may be difficult to handle due to the static electricity. It may be desirable to rehumidify the crosslinked hydrophilic resins to reduce or eliminate the effect of the static electricity. In another embodiment, the surface of the resin particles may be treated with a known antistatic agent such as polyethylene glycol, glycerin and the like. Methods of humidification of dry resins are well known in the art. In a preferred mode the dry crosslinked hydrophilic resin is contacted with a sufficient amount of water vapor to reduce or eliminate the effects of the static electricity, yet not so much so as to cause the crosslinked hydrophilic resin to agglomerate. Preferably the dry crosslinked hydrophilic resin is humidified with about 1 percent or more by weight of water and more preferably about 5 percent or more by weight of water. Preferably, the dry crosslinked resin is humidified with about 10 percent or less by weight of water and more preferably about 6 percent or less by weight of water. Optionally, the agglomeration prevention or rehydration additives may be added to the crosslinked hydrophilic resin. Such additives are well known in the art and include surfactants and inerts inorganic particles such as silica, see for example U.S. Pat. No. 4,286,082, U.S. Pat. No. 4,734,478 and DE 2706135 (the relevant portions of such patents are incorporated herein by reference).

The use of the crosslinker of this invention and the post heat step result in crosslinked hydrophilic resins with a better balance of properties than previously known crosslinked hydrophilic resins. Particularly at a chosen centrifuge capacity the extractable material level is lower and the absorption under load is higher for the crosslinked hydrophilic resins of the invention when compared to conventional resins. Alternatively at a particular absorption under load level the centrifuge capacity is higher than in conventional resins. The crosslinked hydrophilic resins of this invention are more efficient than prior art resins.

As there is balance between the centrifuge capacity and the amount of extractable materials as against the toughness and absorption under load, it is the objective of this invention to maximize the absorption under load and centrifuge capacity. One measure is to examine the relative ratio of the absorption under load to the centrifuge capacity. The higher this number is, the more successful the invention is in maximizing the properties of the water-absorbent resin. Preferably, this ratio is about 0.5 or greater, more preferably about 0.6 or greater, even more preferably about 0.8 or greater and most preferably about 1.0 or greater. It is also preferred that the resins have an absorption under load of about 20 g/g or greater, more preferably about 25 g/g or greater and most preferably about 30 or greater. It is further preferable that the resins have a percent extractable materials level of about 17 percent by weight of the particle or less, more preferably about 12 percent or less, and most preferably about 8 percent or less. It is also preferred that the resins have a centrifuge capacity of about 25 g/g or more and more preferably about 28 g/g or more.

The crosslinked hydrophilic resins demonstrate a dry feel when swollen with water, excellent rehydration behavior, that is the ability of a swollen resin to accept additional fluid, distribute it throughout the gel volume and finally absorb it. The crosslinked hydrophilic resins also demonstrate low incidence of gel blocking as evidenced by formation of fish eyes and unswollen lumps. Thus when the crosslinked hydrophilic resins of the invention are used in absorbent structures they provide better performance in terms of dry feel when swollen, fluid retention under pressure and minimization of leaks. Generally as the load on a hydrophilic resin is increased the absorption capacity decreases. The crosslinked hydrophilic resins of the invention demonstrate a lower rate of decrease in absorption capacity as the load on the resin increases.

The crosslinked hydrophilic resins of this invention can be used in any use wherein absorption and binding of aqueous based fluids is desired. The absorbent structure comprises a support structure and crosseinked hydrophilic resin particles according to the invention. In one embodiment, the crosslinked hydrophilic resins of this invention are mixed into or attached to a structure of absorbent material such as synthetic or natural fibers or paper based woven or non-woven fibers etc. to form a structure. In such structure the woven or non-woven structure functions as a mechanism for wicking and transporting via capillary action the fluid to the water-absorbent resin particles which bind and retain such fluids. In another embodiment, the absorbent structure comprises one or more layer of the crosslinked hydrophilic resins sandwiched between water permeable support layers. In another embodiment, the crosslinked hydrophilic resins are adhesivized and attached to a support structure as disclosed in Ball WO 91/18092 (relevant portions incorporated herein by reference). Examples of such structures are diapers, adult incontinence structures, sanitary napkins and the like.

SPECIFIC EMBODIMENT OF THE INVENTION

The following examples are included to illustrate the invention, and do not limit the scope of the claims. Unless otherwise stated all parts and percentages are by weight.

RESIN PREPARATION PROCEDURE

The crosslinked hydrophilic resins are prepared in an apparatus having four 300 ml glass reactors equipped with thermometers. A waterbath with a heater which is capable of holding all four reactors simultaneously is used. The use of four reactors allows four simultaneous runs of different crosslinkers or crosslinker levels.

106.5 g of a 20 percent aqueous solution of sodium hydroxode and 32.2 g of ice-water are loaded in the open reactors. 38.3 g of acrylic acid are added dropwise under gentle agitation so as to avoid exceeding a temperature of 30 degrees centigrade. Then 0.07 g of a 40% active solution of diethylene diamine pentacetate in water (VERSENEX* 80, (* Trademark of THE DOW CHEMICAL COMPANY)) are added to the mixture. The appropriate amount of crosslinker is dissolved in 20.7 g acrylic acid for each reaction and the resulting mixtures are added to the previously prepared mixtures in the reactors. After all reactors are loaded, the whole set of reactors is closed and deoxygenation is allowed for 30 minutes by nitrogen bubbling. After that time, nitrogen bubbling is reduced and 0.14 g of a 15 percent hydrogen peroxide aqueous solution, 1 g of a 10 percent sodium persulfate aqueous solution and 0.88 g of a 1 percent ascorbic acid aqueous solution are introduced in sequence to all reactors. Polymerisation starts shortly after introduction of ascorbic acid at a temperature of 24 degrees centigrade.

After the peak temperature is reached (between 90 and 100 degrees centigrade) the glass reactors are dipped in the heating bath for 60 minutes at 70 degrees centigrade. Then the reactor is opened and a gelly mass is collected. The aqueous polymer gel is granulated to particles having a size of between approximately 1 and 5 mm with the aid of a meat mincer (disc holes 5 mm) and a part of it is dried in a hot air stream of 160° C. for approximately 20 min. The polymer is ground in a knife cutter and sieved. The particle size fraction between 0.595 and 0.297 mm (30–50 mesh) is used for performance and quality analysis. For gel strength measurement the fraction 0,177 mm to 0,297 mm (50–80 mesh) is used. The 30–50 mesh fraction is collected and analyzed for 30 minutes centrifuge capacity (CC), g/g absorption under load (AUL), g/g and 16 hour extractables fraction (EXT %).

Performance and quality of the crosslinked hydrophilic resins prepared are measured by the following methods.

CENTRIFUGED CAPACITY 200 mg of water-absorbent resin particles are place within a sealable tea bag (63,5×76.2 mm), immersed for 30 minutes into a 0.9% saline solution and then centrifuged for three minutes at 1600 pm. The weight ratio of saline solution absorbed to water-absorbent resin particles is the absorbency capacity (CC).

ABSORPTION UNDER LOAD

A nylon screen (50×50 mm; 100 mesh) is put on top of perforated metal plate (holes with 5 mm) followed by a filter paper and finally by a stainless steel cylinder, of 26 mm inner diameter, 37 mm outer diameter and a height of 50 mm, whose both ends are open. 167 mg of water-absorbent resin particles are placed into the cylinder and evenly distributed, covered by a non-woven sheet of a diameter of 26 mm and finally pressed down with a teflon piston of 26 mm diameter which carries the weight. The total weight of piston and cylinder is 109.4 g. The metal plate with the product in the cylinder on top is immersed into the 0.9% saline solution such that the nylon screen and the water surface have the same level so that the filter paper and the water-absorbent resin particles are able to absorb water without any static pressure. A soak time of one hour is applied. The plate is removed from the water reservoir and the excess water in the holes of the plate and in the nylon screen is soaked up by paper tissues. Then the weight is removed from the swollen gel and the gel is weighed. The weight ratio of saline solution absorbed under load to water-absorbent resin particles is the absorption under load (AUL).

EXTRACTABLE MATERIALS LEVEL 1 g of water-absorbent resin particles and 185 ml of 0.9% saline solution are placed in an 250 ml jar which is capped and put on a shaker for 16 hours. A part of the extraction solution is filtered. With the aid of a Metrohm Titroprocessor the pH of a defined volume of the liltrate is adjusted to pH 10 by 0.1N NaOH and finally titrated to pH 2.7 by 0.1N hydrochloric acid, to determine the amount of residual monomer which is in the filtrate.

EXAMPLES 1–20

The crosslinkers used are trimethylolpropane triacrylate and trimethylolpropane polyoxyethylene triacrylates with varied amounts of ethyleneoxy units. The crosslinker, concentration of the crosslinker and the results are compiled in Table 1.

Selected crosslinked water absorbent resins having each of the different crosslinkers tested herein are post heated according to the following procedure. Each post heated resin is tested for centrifuge capacity, absorption under load and extractables. The results are compiled in Table 1.

POST HEAT PROCEDURE

The post heating is performed by preheating a zone with a hot air gun. Once the target temperature is reached and stabilized the sample is placed in the zone, a contact thermometer is placed in contact with the sample. The temperature of the sample is monitored until it stabilizes at the target temperature. The sample is maintained at the target temperature for 20 minutes.

TABLE 1

| EXAMPLE | number of EO moles/unit | Level in ppm[6] | Centrifuge capacity (g/g) | Extractables (%) | ext/CC | Centrifuge capacity (g/g)[7] | Absorption[7] under Load (g/g) | Extractables[7] (%) | AUL/CC[7] |
|---|---|---|---|---|---|---|---|---|---|
| 1 | 0[1] | 2000 | 41.3 | 19.2 | 0.46 | 25.0 | 26.4 | 7.5 | 1.06 |
| 2 |  | 3500 | 37.6 | 13.2 | 0.35 |  |  |  |  |
| 3 |  | 5000 | 33.2 | 10.0 | 0.30 |  |  |  |  |
| 4 |  | 6500 | 32.6 | 9.3 | 0.29 |  |  |  |  |
| 5 | 3[2] | 2000 | 41.1 | 17.9 | 0.44 | 26.0 | 26.7 | 7.4 | 1.03 |
| 6 |  | 3500 | 38.2 | 12.9 | 0.38 |  |  |  |  |
| 7 |  | 5000 | 35.6 | 11.8 | 0.33 |  |  |  |  |
| 8 |  | 6500 | 30.1 | 8.6 | 0.29 |  |  |  |  |
| 9 | 9[3] | 2500 | 42.6 | 14.3 | 0.34 | 27.6 | 26.7 | 7.4 | 0.97 |
| 10 |  | 5000 | 37.8 | 11.9 | 0.32 |  |  |  |  |
| 11 |  | 6500 | 27.1 | 10.1 | 0.27 |  |  |  |  |
| 12 |  | 8000 | 35.9 | 8.7 | 0.24 |  |  |  |  |
| 13 | 15[4] | 3500 | 42.2 | 14.7 | 0.35 | 29.9 | 28.7 | 7.5 | 0.96 |
| 14 |  | 5000 | 38.7 | 11.1 | 0.29 |  |  |  |  |
| 15 |  | 6500 | 36.6 | 9.5 | 0.26 |  |  |  |  |
| 16 |  | 8000 | 34.8 | 9.7 | 0.28 |  |  |  |  |
| 17 | 20[5] | 4000 | 42.7 | 12.8 | 0.30 | 27.9 | 28.1 | 7.1 | 1.01 |
| 18 |  | 5500 | 40.4 | 10.3 | 0.26 |  |  |  |  |
| 19 |  | 7000 | 36.7 | 8.4 | 0.23 |  |  |  |  |
| 20 |  | 9000 | 35.9 | 7.9 | 0.22 |  |  |  |  |

[1]. CRAYNOR SR 351 resin
[2]. CRAYNOR CN 454 resin
[3]. SARTOMER RO 208 resin
[4]. CRAYNOR CN 435 resin TABLE 1-continued

| EXAMPLE | number of EO moles/unit | Level in ppm[6] | Centrifuge capacity (g/g) | Extractables (%) | ext/CC | Centrifuge capacity (g/g)[7] | Absorption[7] under Load (g/g) | Extractables[7] (%) | AUL/CC[7] |
|---|---|---|---|---|---|---|---|---|---|

[5]. SARTOMER SR 415 resin
[6]. CONCENTRATION OF CROSSLINKER PRESENT BASED ON ACRYLIC ACID
[7]. AFTER POST HEAT Table 1 demonstrates the use of CRAYNOR CN 435 (a trimethylol propane polyoxy ethylene) triacrylate having 5 ethyleneoxy units per polyethyleneoxy chain is advantageous as regards minimization of extractables at a given absorption capacity. This effect is more apparent for high values of centrifuge capacity i.e. 40 g/g and over.

FIG. 1 is a plot of the ratio of extractables (%) to the centrifuge capacity (g/g) vs the centrifuge capacity (g/g) for each of the experiments performed with crosslinked hydrophilic resins wherein the crosslinkers containing 0, 3 and 15 moles of ethylene oxide residue per mole. FIG. 1 demonstrates that hydrophilic resins prepared using a crosslinker having 15 moles of ethylene oxide incorporated into each mole demonstrates lower extractable levels at each a given centrifuge capacity level as hydrophilic resins using crosslinkers without ethylene oxide or with three moles of ethylene oxide per mole. This demonstrates that the invention allows the preparation of hydrophilic resins with lower extractables without reducing the absorption capacity of the resin.

FIG. 2 is the plot of the ratio of Centrifuge Capacity after post heating (CC(T)) to Centrifuge Capacity before heating (CC(o)) against the number of moles of ethylene oxide in the backbone of the crosslinker. FIG. 2 demonstrates that with post heating the balance of properties improve with an increasing number of moles of ethylene oxide and with post heating.

EXAMPLES 21–34

Two sets of samples of crosslinked hydrophilic resin prepared according to the procedure described hereinbefore are subjected to post heating conditions. For one set of samples the crosslinker is trimethylolpropane triacrylate (no ethylene oxide units) at a level of 2150 ppm, (Resin A) and in the second set the crosslinker is trimethylolpropane polyethyleneoxy triacrylate (5 moles of ethyleneoxide units per polyoxyethylene chain) used at a level of 3050 ppm (Resin B). A sample of each set is heated for 20 minutes at temperatures ranging from 180° to 250° C.

The centrifuge capacity, absorption under load and extractable levels are determined as described previously and compiled in Table 2.

TABLE 2

| Example | Resin | POST HEAT TEMP. T (°C.) | CC (g/g) | AUL (g/g) | EXT (%) | CC/CC(o)[2] % | AUL/[3] AUL(o) | EXT/[4] EXT(o) | AUL/CC | EXT/CC |
|---|---|---|---|---|---|---|---|---|---|---|
| 21 | A[1] | None | 40.9 | 7.8 | 17.6 | — | — | — | 0.19 | 0.43 |
| 22 | B | | 45.5 | 6.3 | 18.4 | — | — | — | 0.14 | 0.40 |
| 23 | A[1] | 180 | 38.1 | 9.6 | 13.3 | 0.93 | 1.23 | 0.76 | 0.25 | 0.35 |
| 24 | B | | 45.0 | 13.5 | 16.0 | 0.99 | 2.14 | 0.86 | 0.3 | 0.35 |
| 25 | A[1] | 190 | 33.9 | 21.9 | 11.0 | 0.83 | 2.81 | 0.63 | 0.65 | 0.32 |
| 26 | B | | 42.1 | 20.3 | 14.3 | 0.93 | 3.2 | 0.77 | 0.48 | 0.34 |
| 27 | A[1] | 200 | 33.2 | 20.0 | 11.2 | 0.81 | 2.56 | 0.64 | 0.60 | 0.34 |
| 28 | B | | 41.3 | 21.8 | 13.4 | 0.91 | 3.46 | 0.73 | 0.53 | 0.32 |
| 29 | A[1] | 210 | 27.6 | 23.8 | 9.4 | 0.67 | 3.05 | 0.53 | 0.86 | 0.34 |
| 30 | B | | 39.2 | 26.3 | 12.6 | 0.86 | 4.17 | 0.68 | 0.67 | 0.32 |
| 31 | A[1] | 220 | 25.8 | 24.9 | 7.7 | 0.63 | 3.19 | 0.44 | 0.96 | 0.30 |
| 32 | B | | 36.2 | 29.6 | 11.3 | 0.80 | 4.7 | 0.61 | 0.82 | 0.31 |
| 33 | A[1] | 230 | 25.5 | 26.7 | 7.1 | 0.62 | 3.42 | 0.40 | 1.05 | 0.28 |
| 34 | B | | 34.9 | 31.3 | 10.7 | 0.77 | 4.97 | 0.58 | 0.90 | 0.31 |

[1]. Not an example of the invention.
[2]. Ratio of Centrifuge capacity after post heat to centrifuge capacity before post heating (CC(o)).
[3]. Ratio of absorption under load after post heating to absorption under load before post heating (AUL(o)).
[4]. Ratio of extractables after post heating to extractables before post heating (EXT(o)).

FIG. 3 is a plot of the ratio of CC(T)/CC(O) versus temperature from 180° C. to 230° C., for Resin A and Resin B. CC(T) is the centrifuge capacity after post heating and CC(O) is the centrifuge capacity prior to post heating. FIG. 3 demonstrates that a hydrophilic resin crosslinked with a crosslinker of the invention (15 moles ethylene oxide unit) is less heat sensitive than the resins crosslinked with a prior art crosslinker (0 moles ethylene oxide) because with increasing post heat temperature the CC(T)/CC(o) ratio decreases at a faster rate for prior art resins than for resins crosslinked with crosslinkers of the invention. FIG. 4 shows a plot of the ratio AUL(T)/AUL(O) for Resin A and Resin B at temperatures from 180° to 230° C. AUL (T) is the absorption under load after post heating at the designated temperature and AUL (0) is the absorption under load before post heating. FIG. 4 demonstrates that the absorption under load for Resin B is higher at each temperature than that of Resin A. The increase in absorption under load is greater for Resin B than Resin A as the temperature of post heating increases. FIGS. 3 and 4 combined show that Resin B demonstrates a greater increase in absorption under load and a lower decrease in centrifuge capacity at each temperature than demonstrated by Resin A. FIG. 5 plots the absorption under load against the centrifuge capacity for both Resin A and Resin B at each post heat temperatures. The curve demonstrates that Resin B has a significantly better balance of properties than Resin A. At a selected AUL Resin B demonstrates higher centrifuge capacity (absorption capacity) than Resin A. Alternatively at a selected centrifuge capacity Resin B demonstrates a higher AUL than Resin A. FIG. 6 plots the ratio of absorption under load (AUL) to centrifuge capacity (CC) against the centrifuge capacity of Resin A and B at each post heat temperature. FIG. 6 demonstrates at a selected centrifuge capacity the ratio of absorption under load to centrifuge capacity is higher for Resin B than for Resin A. FIGS. 3 to 6 collectively demonstrate that the use of the crosslinkers of the invention allows a significant improvement in absorption under load by post heating the resin with a smaller reduction in centrifuge capacity (absorption capacity) than demonstrated by resins crosslinked with a prior art crosslinker (Resin A). FIG. 7 plots the level of extractables of Resins A and B at each post heat temperature against centrifuge capacity. FIG. 8 plots the ratio of extractable to centrifuge capacity against centrifuge capacity for Resin A and Resin B at each post heat temperature. FIGS. 7 and 8 demonstrate that the use of the crosslinker of this invention (Resin B) allows higher centrifuge capacity at a given extractable level than a resin which uses a prior art crosslinker (Resin A).

EXAMPLE 35

A sample of hydrophilic resin crosslinked with 3050 ppm of trimethylol propane polyoxyethylene triacrylate (15 moles of ethylene oxide units) is post heated for 20 minutes at 230° C. as previously described, (Resin C). A hydrophilic resin crosslinked with 2150 ppm of trimethlyol propane triacrylate (no ethylene oxide) is post heated for 20 minutes at 190° C. (Resin D). The absorption under load after 60 minutes for Resin C is 31.3 g/g. The absorption under load for Resin D after 60 minutes is 21.9 g/g. The absorption under load (AUL) after various absorption times are measured for both samples. The results are plotted in FIG. 9. FIG. 10 plots the ratio of AUL (t) after 60 minutes against the time for Resins C and D. FIGS. 9 and 10 demonstrate that the rate of absorption of Resin C is faster than that of Resin D. Thus the crosslinked hydrophilic resins of the invention (Resin C) absorb fluids faster and retain fluids better under load than resins crosslinked with a prior art crosslinker (Resin D).

EXAMPLE 36

A hydrophilic resin crosslinked with 8000 ppm trimethylolpropane polyoxyethylene triacrylate (15 moles of ethyleneoxide units) is heated for 10 minutes at 215° C. as previously described (Resin E). Resin E has an initial centrifuge capacity of before post heating of 35 g/g and a final centrifuge capacity of 29 g/g. A second hydrophilic resin crosslinked with trimethylolpropane triacrylate 6500 ppm (0 moles of ethylene oxide) which is not post heated and has centrifuge capacity of 29.4 g/g is also used (Resin F). Both resins are tested for absorption under load (AUL) at several times during a 1 hour period. Resin E shows on AUL of 29.6 g/g after 1 hour and Resin F shows on AUL of 22.3 g/g after 1 hour. The results are plotted in FIG. 11. FIG. 12 plots the ratio of AUL at various times to the AUL after 1 hour against the time for both Resin E and F. FIG. 12 demonstrates that resins of the invention show faster absorption and better fluid retention than prior art resins (Resin F). The AUL of Resins E and F are measured under varying loads of from 0 to 1.0 psi. FIG. 13 demonstrates the results in graphic form.

EXAMPLE 37

100 g of crosslinked hydrophilic resin crosslinked with 8000 ppm trimethylolpropane polyoxyethylene triacrylate (15 moles of ethyleneoxide units) and having a CC of 35 g/g and 9.7% extractables in the powder form is carefully mixed with a formulation consisting in 300 mg Polyoxyethylene—20—sorbitol lanolin derivate (Tradename given by ICI is 61425) and 9 g iso-propanol and 1.5 g water to coat the surface of the resin particles with the formulation. The coated resin is subjected to the post heat treatment, at 170° C. for 10 minutes. The resin obtained has a CC of 33.5 g/g, an AUL of 30.2 g/g and a extractables concentration of 8.4%.

EXAMPLE 38

100 g crosslinked hydrophilic resin crosslinked with 3500 ppm trimethylol propane polyoxyethylene triacrylate (15 moles of ethylene oxide units) with a CC of 41.5 g/g and a extractables concentration of 14.7% in the powder form is carefully mixed with a formulation consisting of 300 mg Glycerine, 150 mg polyoxyethylene—20—sorbitol lanolin derivative and 750 mg water to coat the surface of the particles. The coated resin is post-heated as previously described for 10 minutes at 210° C. The resin obtained has a CC of 30.6 g/g, a AUL of 29.5 g/g and 11.1% extractables.

What is claimed is:

1. A process for the preparation of a crosslinked hydrophilic resin which comprises A) contacting i) one or more of an ethylenically unsaturated carboxylic acid, an ethylenically unsaturated acid anhydride or a salt thereof and optionally ii) one or more of an acrylamide, a vinyl pyrrolidone, a vinyl sulphonic acid, an acrylonitrile, and a polyvinyl alcohol with iii) a crosslinking compound in an aqueous medium, optionally in the presence of a free radical or redox catalyst system, under conditions such that a crosslinked hydrophilic resin is prepared, wherein the crosslinking compound is a compound of the formula

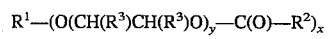

wherein each $R^1$ is independently a polyvalent $C_{2-10}$ straight or branched chain alkyl moiety;

each $R^2$ is independently a $C_{2-10}$ straight or branched chain alkenyl moiety;

each $R^3$ is independently hydrogen or methyl;

each x is independently about 2 or more;

when x is 2, each y is independently from about 3 to about 8; and when x is 3 or more, each y is independently from about 2 to about 7;

B) recovering the crosslinked hydrophilic resin in the form of a hydrogel from the reactor;

C) drying the hydrogel of the crosslinked hydrophilic resin at a temperature sufficient to substantially remove the remaining water and water miscible solvent present in the hydrogel of the hydrophilic resin;

D) optionally, reducing the particle size of the dried hydrophilic resin by mechanical means; and, E) submitting the crosslinked hydrophilic resin particles to a post-heat treatment by heating the crosslinked hydrophilic resin particles under conditions such that the crosslinked hydrophilic resin exhibits a centrifuge capacity of about 25 g/g or greater, an absorption under load of about 25 g/g or greater and a ratio of absorption under load to centrifuge capacity of about 0.6 or greater.

2. A process according to claim 1 wherein the heating temperature is from about 170° to about 250° C. and the heating time is from about 1 to about 60 minutes.

3. A process according to claim 2 wherein the carboxyl containing hydrophilic resin comprises a polymer of i) one or more of an ethylenically unsaturated carboxylic acid, an ethylenically unsaturated carboxylic acid anhydride or a salt thereof and optionally ii) one or more comonomers of an acrylamide, a vinyl pyrrolidone, a vinyl sulphonic acid, an acrylonitrile, a cellulosic monomer, a modified cellulosic monomer, a polyvinyl alcohol monomer or a starch hydrolyzate monomer.

4. A process according to claim 3 wherein each $R^1$ is a $C_{3-6}$ straight or branched chain alkyl moiety;

each $R^2$ is a $C_{2-4}$ straight or branched chain alkenyl moiety;

each $R^3$ is hydrogen;

each x is from about 2 to about 4; and, each y is from about 3 to about 7.

5. A process according to claim 4 wherein the the crosslinking agent is present in an amount of from about 1,000 to about 50,000 parts per million by weight based on the weight of the monomers.

6. A process according to claim 5 wherein the monomer i) is acrylic or methacrylic acid or a salt thereof.

7. A crosslinked hydrophilic resin product prepared by a process which comprises A) contacting i) one or more of an ethylenically unsaturated carboxylic acid, an ethylenically unsaturated acid anhydride or a salt thereof and optionally ii) one or more of an acrylamide, a vinyl pyrrolidone, a vinyl sulphonic acid, an acrylonitrile, and a polyvinyl alcohol with iii) a crosslinking compound in an aqueous medium, optionally in the presence of a free radical or redox catalyst system, under conditions such that a crosslinked hydrophilic resin is prepared, wherein the crosslinking compound is a compound of the formula $$R^1O(O(CH(R^3)CH(R^3)O)_y-C(O)-R^2)_x$$

wherein
each $R^1$ is independently a polyvalent $C_{2-10}$ straight or branched chain alkyl moiety;

each $R^2$ is independently a $C_{2-10}$ straight or branched chain alkenyl moiety;

each $R^3$ is independently hydrogen or methyl;

each x is independently about 2 or more;

when x is 2, each y is independently from about 3 to about 8; and when x is 3 or more, each y is independently from about 2 to about 7;

B) recovering the crosslinked hydrophilic resin in the form of a hydrogel from the reactor;

C) drying the hydrogel of the crosslinked hydrophilic resin at a temperature sufficient to substantially remove the remaining water and water miscible solvent present in the hydrogel of the hydrophilic resin are substantially removed;

D) optionally, reducing the particle size of the dried hydrophilic resin by mechanical means; and, E) submitting the crosslinked hydrophilic resin particles to a post-heat treatment by heating the crosslinked hydrophilic resin particles under conditions such that the crosslinked hydrophilic resin exhibits a centrifuge capacity of about 25 g/g or greater, an absorption under load of about 25 g/g or greater and a ratio of absorption under load to centrifuge capacity of about 0.6 or greater.

8. A crosslinked hydrophilic resin prepared by process according to claim 7 wherein the heating temperature is from about 170° to about 250° C. and the heating time is from about 1 to about 60 minutes.

9. A crosslinked hydrophilic resin prepared by process according to claim 8 which exhibits a centrifuge capacity of about 25 g/g or greater, an absorption under load of about 25 g/g or greater and a ratio of absorption under load over centrifuge capacity of about 0.6 or greater.

10. An absorbent structure comprising a support structure and crosslinked hydrophilic resin particles according to claim 7.

* * * * *